US005756778A

United States Patent [19]
Thiele et al.

[11] Patent Number: 5,756,778
[45] Date of Patent: May 26, 1998

[54] PROCESS FOR PREPARING AN EPOXIDE USING A STRUCTURED CATALYST INCLUDING MICROPOROUS OXIDES OF SILICON, ALUMINUM AND TITANIUM

[75] Inventors: Georg Thiele, Hanau; Eckehart Roland, Bruchkoebel, both of Germany

[73] Assignee: Degussa Aktiengesellschaft, Frankfurt am Main, Germany

[21] Appl. No.: 415,310

[22] Filed: Apr. 3, 1995

Related U.S. Application Data

[62] Division of Ser. No. 274,198, Jul. 12, 1994, Pat. No. 5,525,563.

[30] Foreign Application Priority Data

Jul. 12, 1993 [DE] Germany .......................... 43 23 255.8
Jun. 1, 1994 [DE] Germany .......................... 44 19 195.2

[51] Int. Cl.$^6$ ..................... C07D 301/12; C07D 303/04
[52] U.S. Cl. ............................................................. 549/531
[58] Field of Search ................................................ 549/531

[56] References Cited

U.S. PATENT DOCUMENTS

| | | | |
|---|---|---|---|
| 3,535,225 | 10/1970 | Jaffe . | |
| 3,702,886 | 11/1972 | Argauer et al. . | |
| 3,709,979 | 1/1973 | Chu . | |
| 4,061,724 | 12/1977 | Grose et al. . | |
| 4,073,865 | 2/1978 | Flanigen et al. . | |
| 4,824,976 | 4/1989 | Clerici et al. | 549/531 |
| 4,833,260 | 5/1989 | Neri et al. | 549/531 |
| 4,859,785 | 8/1989 | Bellussi et al. | 549/531 |
| 5,262,550 | 11/1993 | Crocco et al. | 549/531 |
| 5,412,122 | 5/1995 | Saxton et al. | 549/531 |
| 5,453,511 | 9/1995 | Saxton | 549/531 |

FOREIGN PATENT DOCUMENTS

| | | |
|---|---|---|
| 0055044 A1 | 6/1982 | European Pat. Off. . |
| 0118632 A1 | 9/1984 | European Pat. Off. . |
| 0100119 B1 | 9/1986 | European Pat. Off. . |
| 0200260 A2 A3 | 12/1986 | European Pat. Off. . |
| 0112006 B1 | 1/1987 | European Pat. Off. . |
| 0208311 A2 A3 | 1/1987 | European Pat. Off. . |
| 0293950 A1 | 12/1988 | European Pat. Off. . |
| 0299430 | 1/1989 | European Pat. Off. . |
| 0208311 B1 | 1/1991 | European Pat. Off. . |
| 0412596 A1 | 2/1991 | European Pat. Off. . |
| 33 09 669 | 9/1983 | Germany . |
| 30 47 798 | 10/1986 | Germany . |
| 21 19 723 | 8/1987 | Germany . |
| PCT/WO85/04854 | 11/1985 | WIPO . |

OTHER PUBLICATIONS

Meier, Walter M., *Atlas of Zeolite Structure Types*, 2nd Edition, 1987, pp. 586–587, 592–593.

Bibby, D.M., et al., "Silicalite-2, A Silica Analogue of the Aluminosilicate Zeolite ZSM-11", *Nature*, vol. 280, Aug. 23, 1979, pp. 664–665.

Sudhakar Reddy, J., et al., "Selective Oxidation of n-Hexane Over a Titanium Silicate Molecular Sieve with MEL Structure", *Journal of Molecular Catalysis*, 70 (1991), pp. 335–342.

Sudhakar Reddy, J., et al., "Ammoximation of Cyclohexanone Over a Titanium Silicate Molecular Sieve, TS-2", *Journal of Molecular Catalysis*, 69 (1991), pp. 383–392.

Clerici, Mario G., et al., "Epoxidation of Lower Olefins with Hydrogen Peroxide and Titanium Silicalite", *Journal of Catalysis*, 140 (1993), pp. 71–83.

Sudhakar Reddy, J., et al., "Titanium Silicate-2: Synthesis, Characterization and Catalytic Properties", *Applied Catalysis*, 58 (1990), pp. L1–L4.

*Primary Examiner*—Joseph E. Evans
*Attorney, Agent, or Firm*—Beveridge, DeGrandi, Weilacher & Young, L.L.P.

[57] ABSTRACT

A catalyst includes or consists essentially of the oxides of silicon, aluminum and titanium, characterized in that the catalyst particles are built up from a core with the composition $(SiO_2)_x(AlO_2)_yM_y$, wherein $x/y=10$ to $\infty$ and M=H, Na, K, $NH_4$, or $NR_4$, wherein R is a $C_{1-8}$-alkyl, and a shell with the composition $(SiO_2)_n(TiO_2)_m$, wherein $n/m=12$ to 1000. Both the core and the shell have a crystal structure of MFI or MEL. The catalyst can be prepared by preparing a synthesis gel for the preparation of a titanium silicalite, thereafter introducing an aluminosilicate of the MFI or MEL structural type into this synthesis gel, and working up the synthesis gel in a known manner to obtain the product.

4 Claims, 8 Drawing Sheets

FIG. 1A
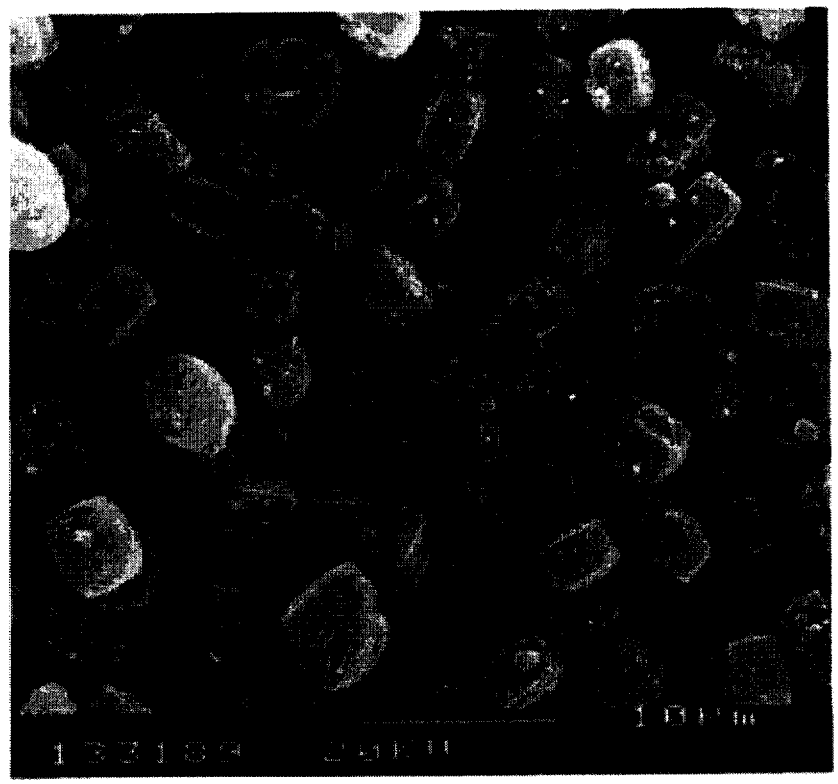
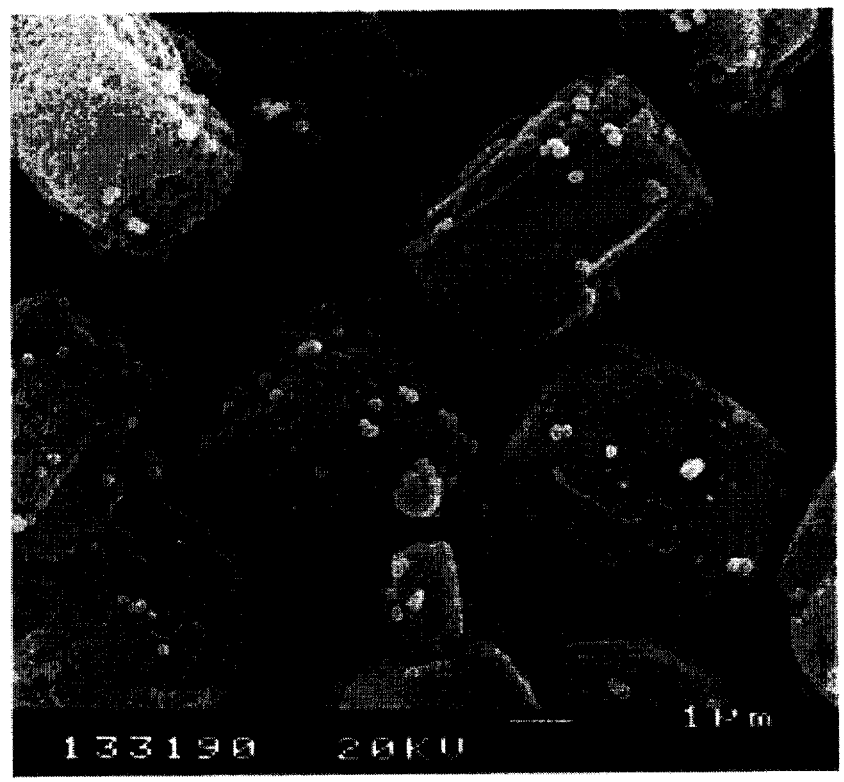
FIG. 1B

FIG. IC
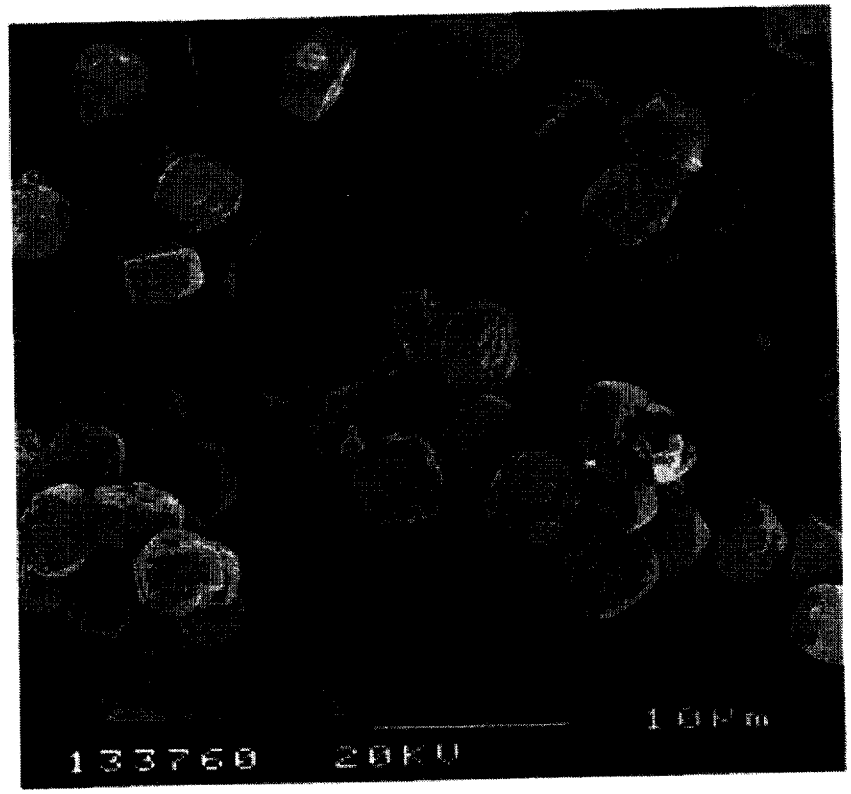
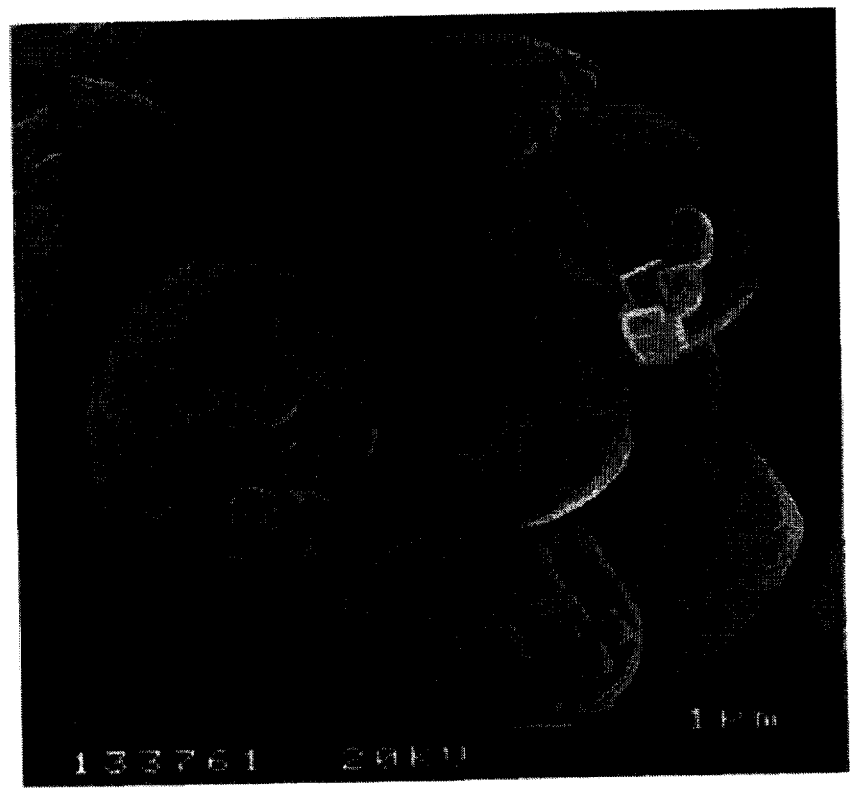
FIG. ID

PROCESS FOR PREPARING AN EPOXIDE USING A STRUCTURED CATALYST INCLUDING MICROPOROUS OXIDES OF SILICON, ALUMINUM AND TITANIUM

This application is a divisional of application Ser. No. 08/274,198 filed on Jul. 12, 1994, now U.S. Pat. No. 5,525,563, which application is entirely incorporated herein by reference.

BACKGROUND OF THE INVENTION

The invention relates to a structured catalyst including microporous oxides of silicon, aluminum and titanium, and a process for producing this catalyst.

Microporous aluminosilicates of the structural type MFI (ZSM-5) and MEL (ZSM-11), and methods for producing them by hydrothermal synthesis are known from U.S. Pat. No. 3,702,886 and DE 21 19 723. These patent documents are entirely incorporated herein by reference. The structural types MFI and MEL are also described in W. M. Meier and D. H. Olson, *Atlas of Zeolite Structure Types*, Butterworth-Heinemann, 1992, which is also entirely incorporated herein by reference. Aluminum-free materials with identical structures, known as silicalite-1 and silicalite-2, are disclosed in U.S. Pat. No. 4,073,865; U.S. Pat. No. 4,061,724; D. M. Bibby, N. B. Milestone, and L. P. Aldridge, *Nature* 280, 664 (1979); and European Patent Appl. No. 112,006. These documents also are entirely incorporated herein by reference. Materials in which some of the silicon atoms in the silicalite-1 or silicalite-2 structures are replaced by titanium atoms are known as titanium silicalites TS-1 and TS-2 and are described in DE 30 47 798 and J. S. Reddy, R. Kumar, and P. Ratnasamy, Appl. Catal., 58 (1990) L1–L4. These documents also are entirely incorporated herein by reference. Titanium silicalites are efficient catalysts for selective oxidation using hydrogen peroxide, in particular for the epoxidation of olefins (European Patent Appl. No. 100,119), the hydroxylation of aromatic compounds (DE 33 09 669 and J. S. Reddy, R. Kumar, and P. Ratnasamy, Appl. Catal., 58 (1990) L1–L4), the hydroxylation of aliphatic compounds (European Patent Appl. No. 412,596 and J. S. Reddy, S. Sivasanker, and P. Ratnasamy, J. Mol. Catal., 70 (1991) pp. 335–342) and the ammoximation of cyclohexanone (European Patent Appl. No. 208,311 and J. S. Reddy, S. Sivasanker, and P. Ratnasamy; J. Mol. Catal., 69 (1991) pp. 383–392). All of these documents are entirely incorporated herein by reference.

The known preparation of titanium silicalites TS-1 and TS-2 proceeds via a two-stage synthesis. First, a gel is produced by hydrolysis of a source of titanium, such as $TiCl_4$, $TiOCl_2$ or $Ti(Oalkyl)_4$, preferably $Ti(Oalkyl)_4$, and a source of silicon, such as silica gel or $Si(Oalkyl)_4$, preferably $Si(Oalkyl)_4$. Then this gel is crystallized in a hydrothermal synthesis by heating under pressure, wherein a template has to be added to promote crystallization, such as tetra-n-propylammonium hydroxide for TS-1 or tetra-n-butylammonium hydroxide for TS-2. The high price of $Ti(Oalkyl)_4$, $Si(Oalkyl)_4$ and the templates contribute greatly to the cost of producing TS-1 and TS-2.

The titanium silicalites TS-1 and TS-2 are mostly produced in the form of small crystallites with sizes of less than one micrometer in the known processes. These crystallites can only be separated from the liquid with difficulty by filtering. For industrial application of these materials, therefore, an additional agglomeration step is required. An example of such an agglomeration procedure is described in European Patent Appl. No. 203,260, which document is entirely incorporated herein by reference.

When using titanium silicalites TS1 and TS2 as catalysts for oxidation reactions using hydrogen peroxide, the catalytic activity is determined by the molecular size and molecular structure of the compound to be oxidized (M. Clerici and P. Ingallina, J. Catal., 140 (1993) pp. 71–83, which document is entirely incorporated herein by reference). This indicates that there is a restriction on the catalytic activity due to material transport inside the cavities in the crystal lattice, so that titanium atoms in the interior of the crystal contribute less to the catalytic activity than titanium atoms near the surface of the crystal.

There is a need, therefore, for catalysts which exhibit similar activity to titanium silicalites in selective oxidation reactions using hydrogen peroxide, and which can be prepared using small amounts of $Ti(Oalkyl)_4$, $Si(Oalkyl)_4$, and a template, and which enable targeted setting of the crystal size to enable better utilization of the catalytic activity of the titanium atoms.

SUMMARY OF THE INVENTION

The invention provides a catalyst including oxides of silicon, aluminum and titanium which is characterized in that the catalyst particles are composed of a core with the composition $(SiO_2) \cdot (Al_2O_3)_y M_y$, wherein $x/y=10$ to $\infty$ and $M=H$, Na, K, $NH_4$, or $NR_4$, wherein $R=C_{1-8}$-alkyl, and a shell with the composition $(SiO_2)_n (TiO_2)_m$, wherein $n/m=12$–$1000$, and both the core and the shell have a crystal structure of the MFI or MEL type.

In preferred forms of the invention, the catalyst consists of or consists essentially of oxides of silicon, aluminum and titanium.

In particularly preferred embodiments of the invention, the shell on the catalyst has the composition $(SiO_2)_n (TiO_2)_m$ wherein $n/m=20$–$200$.

The catalyst according to the invention can be prepared by preparing a synthesis gel in the same way as is known for preparing titanium silicalite (as shown, for example, in DE 30 47 798 and Reddy et al., supra.), wherein a source of titanium, such as $TiCl_4$, $TiOCl_2$ or $Ti(Oalkyl)_4$, and a source of silicon, such as silica gel or $Si(Oalkyl)_4$, can be mutually hydrolyzed; a tetraalkylammonium hydroxide can be added as a template; a crystalline aluminosilicate, for example, one having the crystal structure of MFI or MEL, such as zeolite ZSM-5 or ZSM-11, can be introduced into this synthesis gel; and the synthesis gel can be worked up in a known manner to obtain the product, for example by crystallizing under hydrothermal conditions, separating, filtering and calcining the crystalline product.

The crystalline aluminosilicate can be added to the raw materials before gel formation, or during the gel formation phase, or to the finished gel before crystallization. When adding the aluminosilicate in the protonated H-form (H-ZSM-5 or H-ZSM-11), this, as an acid component, can initiate precondensation.

BRIEF DESCRIPTION OF THE DRAWINGS

The invention will now be described in more detail using several specific examples, which are advantageously considered in conjunction with the attached drawings, wherein:

FIGS. 1a and 1b show scanning electron microscope (SEM) images of the catalyst particles of Example 1 magnified 3000:1 and 10,000:1, respectively;

FIGS. 1c and 1d show scanning electron microscope images of the H-ZSM-5 core material used in Example 1 magnified 3000:1 and 10,000:1, respectively;

DETAILED DESCRIPTION OF THE INVENTION

Figure 2:
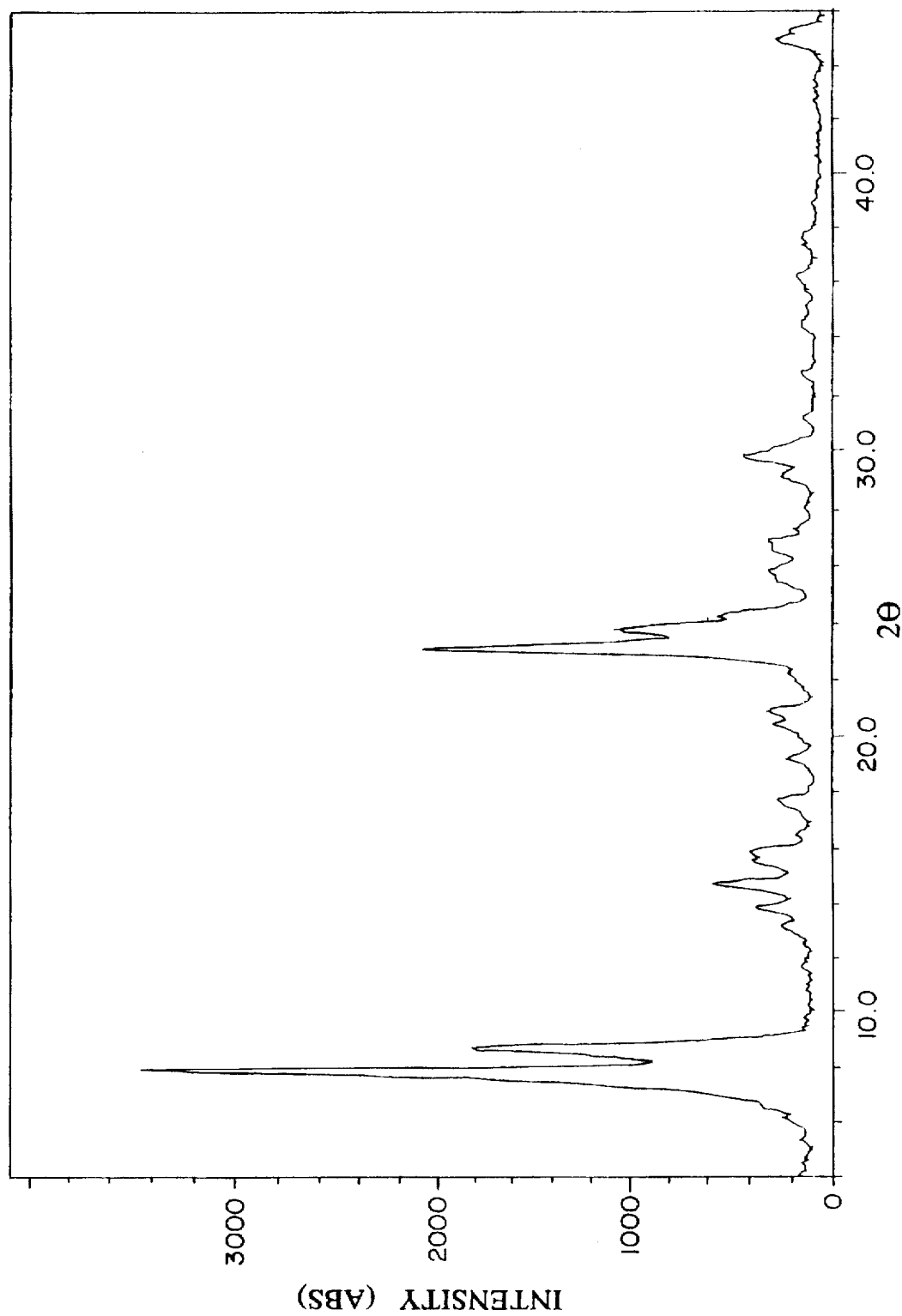
FIGS. 2–5 show X-ray diffraction diagrams for the materials of Examples 1–4, respectively.

The invention will now be described in more detail with the aid of the attached drawings and various specific examples.

A catalyst is provided in accordance with the invention which includes oxides of silicon, aluminum and titanium. The catalyst particles are composed of a core having the following composition:

$$(SiO_2)_x(Al_2O_3)_yM_y,$$

wherein x/y is in the range of 10 to ∞, and

M represents a member selected from the group consisting of H, Na, K, NH$_4$, and NR$_4$, wherein R in the formula "NR$_4$" represents an alkyl having 1–8 carbon atoms (i.e., a C$_{1-8}$-alkyl).

The catalyst particles further include a shell having the following composition:

$$(SiO_2)_n(TiO_2)_m,$$

wherein n/m is in the range of 12 to 1000. Both the core and the shell have a crystal structure of the MFI or MEL type.

In one particularly preferred embodiment of the invention, the core of the catalyst has the composition $(SiO_2)_x(Al_2O_3)_yM_y$, wherein x/y is in the range of 10 to ∞, and the shell has the composition $(SiO_2)_n(TiO_2)_m$, where n/m is in the range of 20 to 200.

The invention also relates to a process for preparing the catalyst having the above-described characteristics. The process for preparing the catalyst includes preparing a synthesis gel for the preparation of a titanium silicalite in a manner that is known in the art. A crystalline aluminosilicate is introduced into this synthesis gel, and the synthesis gel is worked up in a known manner to obtain the product.

In another aspect of the invention, after calcining the catalyst during preparation thereof, the catalyst is neutralized with a base whose pK$_B$ value is between 0 and 11, so that an aqueous suspension of the catalyst has a pH between 5 and 9 after neutralization.

Using the catalyst in accordance with the invention, an epoxide may be prepared by reacting an olefin with hydrogen peroxide in the liquid phase in the presence of the catalyst, and thereafter recovering the epoxide product. Likewise, the catalyst in accordance with the invention may be used in a process for preparing an oxime by reacting a ketone with hydrogen peroxide and ammonia in the liquid phase in the presence of the catalyst, and thereafter recovering the oxime product.

The composition of the synthesis gel for preparing the catalyst as described above, can be selected to provide the following ranges of molar ratios:

SiO$_2$/TiO$_2$=5–1000;
OH$^-$/SiO$_2$=0.1–1.0;
H$_2$O/SiO$_2$=15–200, preferably 20 to 200; and
NR$_4^+$/SiO$_2$=0.1–2.0.

The ratio of the amount of SiO$_2$ and TiO$_2$ contained in the synthesis gel to the amount of crystalline aluminosilicate added to the synthesis gel can be selected to be within the range of 0.02 to 20 by weight.

The catalyst particles prepared in this way show the same morphology and particle sizes as the aluminosilicate added as the core material in a scanning electron microscope image. The average particle diameter is larger than that of the titanium silicalite which is prepared in the absence of the core material. Their X-ray diffraction diagrams, as shown in FIGS. 2 to 5, show the characteristic reflections for crystalline zeolites of the MFI structural type. The bands observed at 960–975 cm$^{-1}$ in the IR spectrum demonstrate the incorporation of isolated titanium atoms into the crystal lattice of the material.

Figure 6:
FIG. 6 is a transmission electron microscope (TEM) image of a section of the catalyst particles according to Example 1, with an E-magnification of 20,000 and a total magnification of 100,000:1.

Transmission electron microscope images of sections of the catalyst particles according to the invention (FIGS. 6 and 7) show the structure of the catalyst particles consisting of a closed shell on the core material used. X-ray photoelectron spectroscopy (XPS) of the catalyst particles shows that the surface of the catalyst particles contains only titanium and silicon, and no aluminum. After wearing away some of the catalyst surface by sputtering, the amount of titanium detected by XPS decreases considerably, and the aluminum contained in the core of the particles is detected. This indicates that the catalysts according to the invention have a structure comprising a core which essentially has the composition of the aluminosilicate used to prepare the catalyst, and a shell with the composition $(SiO_2)_n(TiO_2)_m$.

The invention has the advantage, as compared with the prior art, that, in the catalyst according to the invention, the catalytically active titanium atoms are intentionally incorporated into a layer at the surface of the crystal, wherein the thickness of this layer can be controlled by selecting the conditions of preparation. The requirement for expensive starting materials is reduced, as compared with the prior art, due to this method of preparation. By using initial crystals of specific sizes, larger catalyst particles can be produced without additional agglomeration steps, the size of the catalyst particles being predetermined by selecting the size of the initial crystals and selecting the conditions of synthesis.

The catalyst according to the invention can be used for selective oxidation using H$_2$O$_2$ in the liquid phase, for example for ammoximation of ketones, such as cyclohexanone or cyclododecanone, or for the epoxidation of olefins, such as propene, 1-butene, 2-butene, 1-pentene, allyl chloride or allyl alcohol. The products from such reactions can be recovered in any conventional manner known to those skilled in the art.

When used to prepare acid-sensitive products, such as epoxides, the catalyst can be neutralized after calcination by treating it with a base having a pK$_B$ value between 0 and 11, preferably an aqueous solution of sodium acetate, sodium carbonate, sodium bicarbonate or ammonia, so that an aqueous solution of the catalyst after neutralization has a pH between 5 and 9.

EXAMPLES

The invention will now be described in various specific Examples. These Examples should be construed as illustrating the invention, and not as limiting the same.

Preparation of the catalyst

Example 1

37.2 ml of Si(OEt)$_4$ are diluted with 44.4 ml of absolute i-propanol in a stirred flask (500 ml) provided with a stirrer, thermometer and reflux condenser. The admission of atmospheric moisture into the flask is prevented by a $CaCl_2$ tube. Then 2.8 ml of Ti(O n-Bu)$_4$ in 8.5 ml of absolute i-propanol at room temperature are added dropwise with stirring. Finally 23.8 g of H-ZSM-5 ($SiO_2/Al_2O_3$=67, $d_{50}$=7.6 μm), which was first calcined at 550° C. for 1 hour, is added. The resulting suspension is heated for two hours under reflux. After cooling to room temperature, 42.5 ml of a 20 wt. % strength aqueous solution of tetra-n-propylammonium hydroxide are added dropwise over the course of 10 minutes, wherein the mixture warms up slightly. The flask is then provided with a distillation bridge. The mixture of alcohols, i-propanol, ethanol, n-butanol, and some water, are distilled off. 86 ml of water is added to the resulting residue and agitated. To crystallize, this mixture is transferred to an autoclave (500 ml) provided with a stirrer and lined with Teflon® (a polytetrafluorethylene coating available from the E.I. DuPont de Nemours Company) and heated to 180° C. for 22 hours. The solid obtained is isolated by centrifuging, washed with two portions of 50 ml of distilled water, dried at 120° C. and calcined at 550° C. for 10 hours. Finally, the product is treated for 1 hour at 80° C. with 150 ml of a 10 wt. % aqueous ammonium acetate solution, centrifuged off, washed with two portions of 50 ml of distilled water, dried at 120° C. and calcined at 550° C. for 10 hours.

The composition of the catalyst prepared in this way, determined-by wet analysis, is: $TiO_2$: 1.6 wt. %; $SiO_2$: 96.8 wt. %; and $Al_2O_3$: 1.6 wt. %.

The X-ray diffraction diagram (FIG. 2) shows that the catalyst consists of crystalline material of the MFI structural type.

The IR spectrum shows a shoulder at 965 cm$^{-1}$, which is characteristic of the incorporation of isolated titanium atoms into the crystal lattice of the material. The scanning electron microscope image of the catalyst particles (magnification 3000:1 (FIG. 1a) and 10,000:1 (FIG. 1b)), as compared with the scanning electron microscope image of the H-ZSM-5 core material used (magnification 3000:1 (FIG. 1c) and 10,000:1 (FIG. 1d)), show that the morphology and particle size of the core material is essentially retained during preparation of the catalyst.

The transmission electron microscope sectional image of a catalyst particle (FIG. 6, magnification 100,000:1) shows a structure having a 0.08–0.15 μm thick, closed shell on the core material.

The surface composition (Si: 30.8 mol. %; Ti: 0.48 mol. %; and Al: not detectable), determined by X-ray photoelectron spectroscopy (XPS), indicates that the shell of the catalyst consists of aluminum-free titanium silicalite. The surface composition found after wearing away the surface by means of sputtering (Si: 34.7 mol. %; Ti: 0.19 mol %; and Al: 0.80 mol. %) indicates that the titanium is essentially contained only in the shell and not in the core of the catalyst.

Example 2

Example 1 is repeated with the difference that 17.8 g of H-ZSM-5 ($SiO_2/Al_2O_3$=150, $d_{50}$=5.7 μm) is used.

The composition of the catalyst prepared in this way, determined by wet analysis, is: $TiO_2$: 2.3 wt. %; $SiO_2$: 96.9 wt. %; and $Al_2O_3$: 0.8 wt. %.

Figure 3:
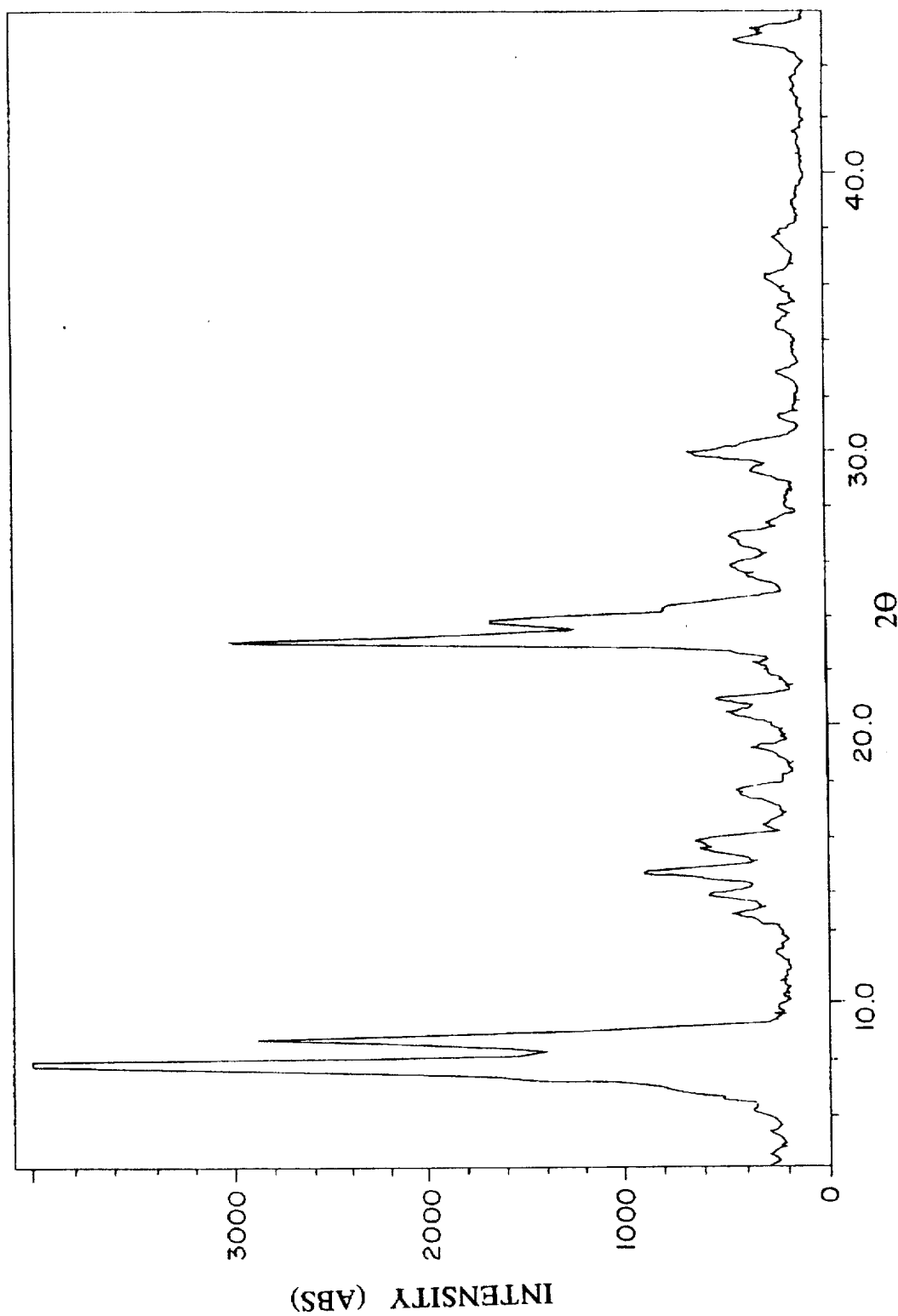

X-ray diffraction diagram: FIG. 3.

IR spectrum: shoulder at 966 cm$^{-1}$.

Example 3

Example 1 is repeated with the difference that 53.5 g of H-ZSM-5 ($SiO_2/Al_2O_3$=ca. 1000, $d_{50}$=16.1 μm) is used.

The composition of the catalyst prepared in this way, determined by wet analysis, is: $TiO_2$: 0.6 wt. %; $SiO_2$: 99.3 wt. %; and $Al_2O_3$: 0.1 wt. %.

Figure 4:
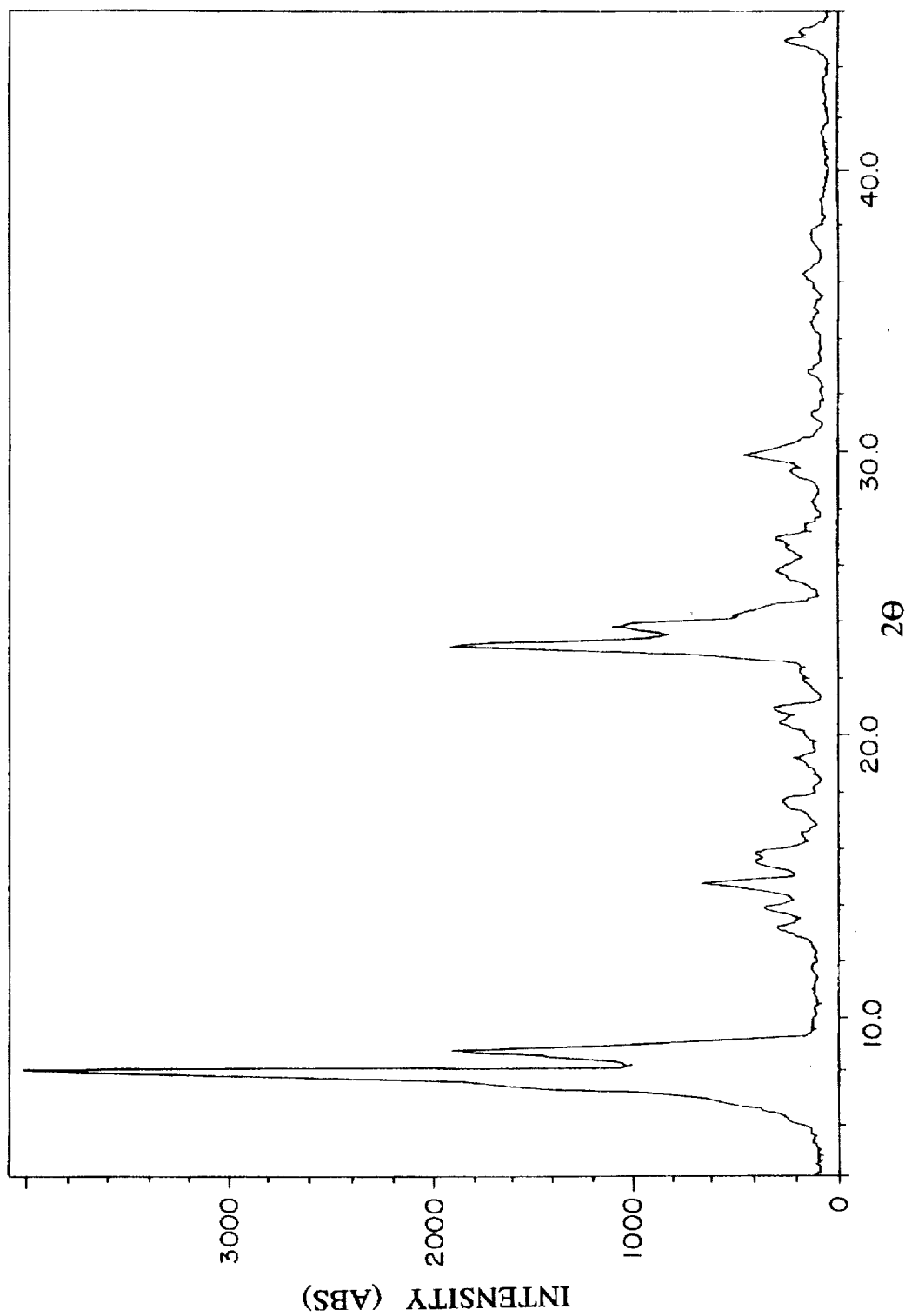

X-ray diffraction diagram: FIG. 4.

Figure 7:
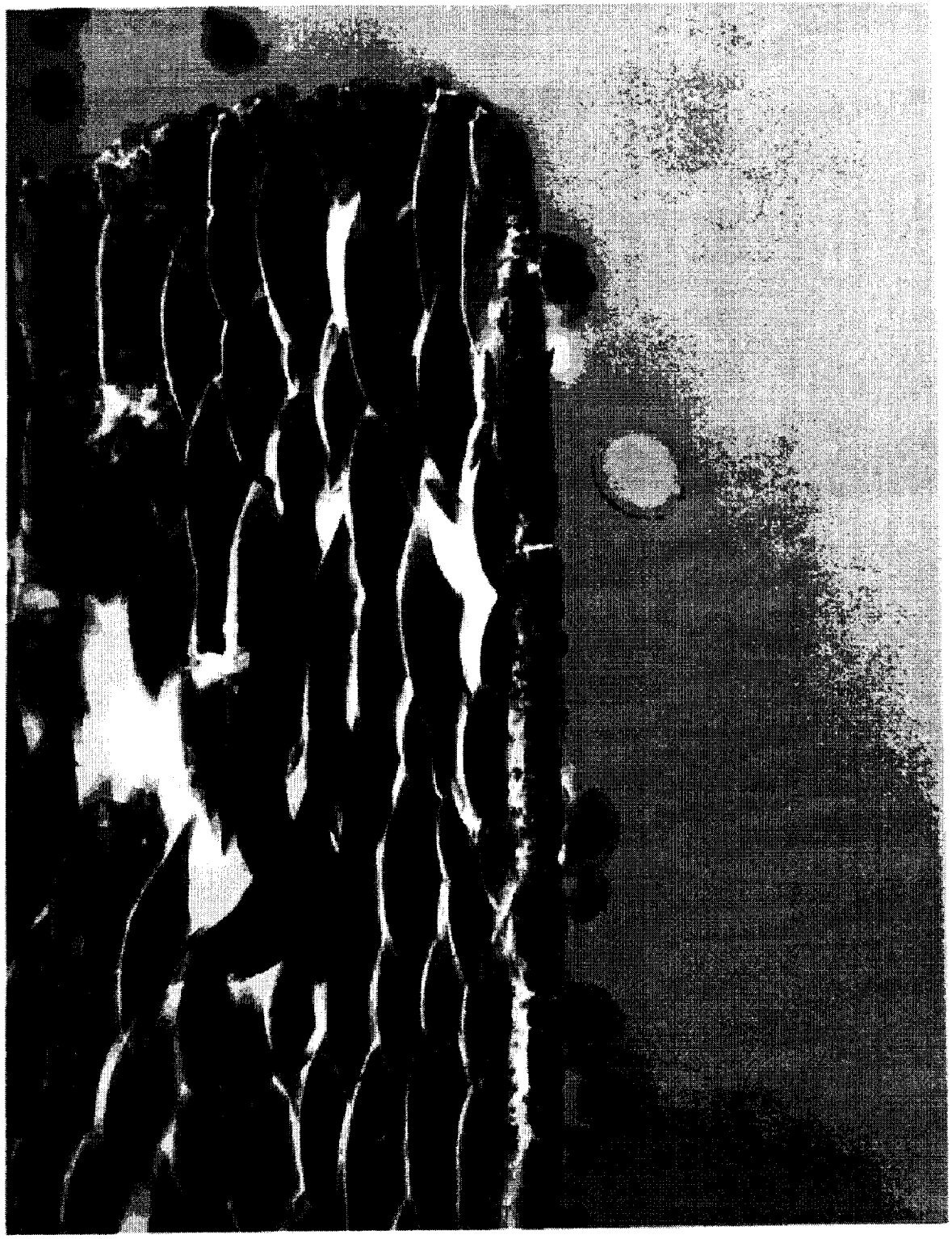
FIG. 7 is a transmission electron microscope image of a section of the catalyst particles according to Example 3, with an E-magnification of 12,000 and a total magnification of 50,000:1.

Transmission electron microscope sectional diagram (magnification 50,000:1): FIG. 7.

Example 4

Example 1 is repeated with the difference that 11.2 g of H-ZSM-5 ($SiO_2/Al_2O_3$=28, $d_{50}$ =3.7 mm) is used.

The composition of the catalyst prepared in this way, determined by wet analysis, is: $TiO_2$: 3.3 wt. %; $SiO_2$: 93.5 wt. %; and $Al_2O_3$: 3.2 wt. %.

Figure 5:
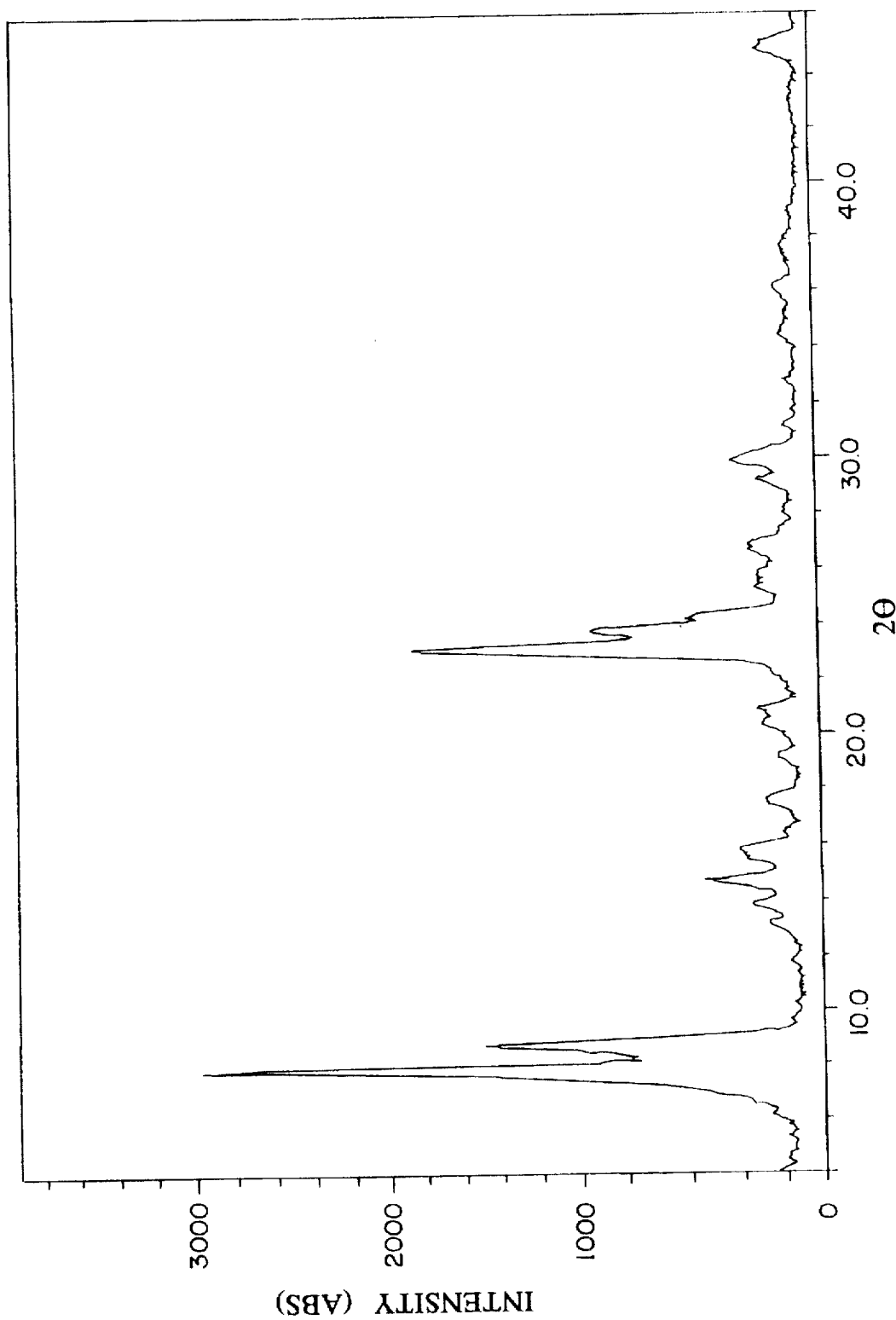

X-ray diffraction diagram: FIG. 5.

IR spectrum: bands at 972 cm$^{-1}$.

Example 5 (Comparison Example)

A non-structured, pure titanium silicalite was synthesized in accordance with Example 1 of German Patent DE 30 47 798 as a comparison catalyst.

The composition of the catalyst prepared in this way, determined by wet analysis, is: $TiO_2$: 2.5 wt. %; and $SiO_2$: 97.5 wt. %.

The following are examples of the ammoximation of cyclohexanone to give cyclohexanonoxime using the catalyst compositions produced above.

Example 6

1.0 gram of catalyst in accordance with Example 1 was initially introduced into a mixture of 17 ml of tert-butanol and 20.5 ml of 14 wt. % strength aqueous ammonia solution in a 100 ml reactor with a double-walled jacket and a pressure retention device. After sealing the apparatus, it is heated to 80° C., and 7.16 ml of cyclohexanone and 7.27 ml of 30% strength aqueous hydrogen peroxide solution are added simultaneously, with stirring, over the course of 5 hours. The mixture is subsequently stirred for 30 minutes at 80° C., then cooled to room temperature, the pressure is released, it is diluted with tert-butanol and filtered. Unconverted hydrogen peroxide is determined by iodometric titration, unconverted cyclohexanone and the cyclohexanonoxime produced are determined using gas chromatography. With a hydrogen peroxide conversion of 99% and a cyclohexanone conversion of 94%, cyclohexanonoxime is formed with a selectivity of greater than 99%, with reference to the cyclohexanone converted.

Example 7

Example 6 is repeated with 1.0 gram of catalyst in accordance with Example 2. With a hydrogen peroxide conversion of 100% and a cyclohexanone conversion of 79%, cyclohexanonoxime is formed with greater than 99% selectivity, with reference to the cyclohexanone converted.

Example 8

Example 6 is repeated with 1.0 gram of catalyst in accordance with Example 3. With a hydrogen peroxide conversion of 99% and a cyclohexanone conversion of 67%, cyclohexanonoxime is formed with greater than 99% selectivity, with reference to the cyclohexanone converted.

Example 9

Example 6 is repeated with 1.0 gram of catalyst in accordance with Example 4. With a hydrogen peroxide conversion of 99% and a cyclohexanone conversion of 82%, cyclohexanonoxime is formed with greater than 99% selectivity, with reference to the cyclohexanone converted.

Example 10

Example 6 is repeated with 0.66 grams of catalyst in accordance with Example 5. With a hydrogen peroxide conversion of 100% and a cyclohexanone conversion of 81%, cyclohexanonoxime is formed with 86% selectivity, with reference to the cyclohexanone converted.

The following are examples of the epoxidation of 1-octene to give 1-octene oxide using untreated catalyst (i.e., a catalyst which is not treated with a base).

Example 11

1.6 grams of catalyst according to Example 1 in a mixture of 60 grams of methanol and 11.6 grams of 1-octene are initially introduced into a 100 ml reactor with a double-walled jacket. The mixture is heated to 55° C. and 3.40 grams of 49 wt. % strength aqueous hydrogen peroxide solution is added with stirring. After stirring for 30 minutes at 55° C., a sample is withdrawn, filtered and analyzed. Unconverted hydrogen peroxide is determined by cerimetric titration, unconverted 1-octene and the oxidation products 1-octene oxide, 1-methoxy-2-octanol and 2methoxy-1-octanol are determined using gas chromatography. With a hydrogen peroxide conversion of 29%, 66% of oxidation products are formed, with reference to the hydrogen peroxide converted. The epoxide selectivity, with reference to the oxidation products formed, is 74%.

Example 12

Example 11 is repeated using 1.1 grams of catalyst according to Example 2. With a hydrogen peroxide conversion of 25%, 78% of oxidation products are formed, with reference to hydrogen peroxide converted. The epoxide selectivity, with reference to the oxidation products formed, is 72%.

Example 13

Example 11 is repeated using 4.0 grams of catalyst according to Example 3. With a hydrogen peroxide conversion of 34%, 67% of oxidation products are formed, with reference to the hydrogen peroxide converted. The epoxide selectivity, with reference to the oxidation products formed, is 69%.

Example 14

Example 11 is repeated using 0.75 grams of catalyst according to Example 4. With a hydrogen peroxide conversion of 21%, 53% of oxidation products are formed, with reference to hydrogen peroxide converted. The epoxide selectivity, with reference to the oxidation products formed, is 44%.

Example 15

Example 11 is repeated using 0.66 grams of catalyst according to Example 5. With a hydrogen peroxide conversion of 21%, 85% of oxidation products are formed, with reference to the hydrogen peroxide converted. The epoxide selectivity, with reference to the oxidation products formed, is 88%.

The following examples relate to neutralizing the catalysts with sodium acetate to thereby produce treated catalysts.

Example 16

5 grams of catalyst according to Example 1 are heated for 20 minutes under reflux with a solution of 1 gram of sodium acetate in 100 ml of deionized water. This is then filtered, the catalyst is washed with hot, deionized water and with methanol, and dried in the air. A suspension of 0.5 grams of the catalyst in 10 ml of deionized water had a pH of 3.7 before neutralization, and a pH of 6.3 after neutralization.

Example 17

Example 16 is repeated with 5 grams of catalyst according to Example 2. A suspension of 0.5 grams of the catalyst in 10 ml of deionized water had a pH of 3.8 before neutralization and a pH of 6.5 after neutralization.

Example 18

Example 16 is repeated with 5 grams of catalyst according to Example 3. A suspension of 0.5 grams of the catalyst in 10 ml of deionized water had a pH of 4.4 before neutralization, and a pH of 6.5 after neutralization.

Example 19

Example 16 is repeated with 5 grams of catalyst according to Example 4. A suspension of 0.5 grams of the catalyst in 10 ml of deionized water had a pH of 3.8 before neutralization, and a pH of 6.6 after neutralization.

Example 20

Example 16 is repeated with 5 grams of catalyst according to Example 5. A suspension of 0.5 grams of the catalyst in 10 ml of deionized water had a pH of 5.2 before neutralization, and a pH of 7.7 after neutralization.

The following are examples of the epoxidation of 1-octene to give 1-octene oxide using the neutralized catalysts (i.e., treated catalysts).

Example 21

Example 11 is repeated with 1.6 grams of the catalyst according to Example 16. With a hydrogen peroxide conversion of 30%, 84% of oxidation products are formed, with reference to the hydrogen peroxide converted. The epoxide selectivity, with reference to the oxidation products formed, is 92%. Thus, the selectivity is higher than when using non-neutralized catalyst from Example 1 (see also Example 11).

Example 22

Example 11 is repeated with 1.1 grams of the catalyst according to Example 17. With a hydrogen peroxide conversion of 29%, 85% of oxidation products are formed, with reference to the hydrogen peroxide converted. The epoxide selectivity, with reference to the oxidation products formed, is 89%. Thus, the selectivity is higher than when using non-neutralized catalyst according to Example 2 (see also Example 12).

Example 23

Example 11 is repeated with 4.0 grams of the catalyst according to Example 18. With a hydrogen peroxide conversion of 35%, 92% of oxidation products are formed, with reference to the hydrogen peroxide converted. The epoxide selectivity, with reference to the oxidation products formed, is 88%. Thus, the selectivity is higher than when using non-neutralized catalyst from Example 3 (see also Example 13).

Example 24

Example 11 is repeated with 0.76 grams of the catalyst according to Example 19. With a hydrogen peroxide conversion of 20%, 94% of oxidation products are formed, with reference to the hydrogen peroxide converted. The epoxide selectivity, with reference to the oxidation products formed, is 91%. Thus, the selectivity is higher than when using non-neutralized catalyst from Example 4 (see also Example 14).

Example 25

Example 11 is repeated with 0.66 grams of the catalyst according to Example 20. With a hydrogen peroxide conversion of 26%, 100% of oxidation products are formed, with reference to the hydrogen peroxide converted. The epoxide selectivity, with reference to the oxidation products formed, is 98%.

By the expression "crystal structure of MFI or MEL", as used herein, is meant structures of the type disclosed in U.S. Pat. No. 3,702,886 and Meier et al., *Atlas of Zeolite Structure Types*, supra.

While the invention has been described in terms of various specific examples, those skilled in the art will appreciate that various changes and modifications may be made without departing from the spirit and scope of the invention, as defined in the claims.

The priority applications, German Patent Appl. Nos. P 43 23 255.8 and P 44 19 195.2, filed in Germany on Jul. 12, 1993 and Jun. 1, 1994, respectively, are entirely incorporated herein by reference.

We claim:

1. A process for preparing an epoxide, comprising:
   reacting an olefin with hydrogen peroxide in a liquid phase in the presence of a catalyst which includes catalyst particles with a core having a composition as follows:

$$(SiO_2)_x(Al_2O_3)_yM_y$$

wherein x/y is in the range of 10 to 150,

M represents a member selected from the group consisting of: H, Na, K, NH$_4$, and NR$_4$ wherein R is an alkyl group having 1 to 8 carbon atoms, and a shell over the core, wherein the shell has a composition as follows:

$$(SiO_2)_n(TiO_2)_m$$

wherein n/m is in the range of 12 to 1000, wherein both the core and the shell have a crystal structure of MFI or MEL; and recovering the epoxide produced in the reacting step.

2. A process for preparing an epoxide according to claim 1, wherein the shell of the catalyst has the composition $(SiO_2)_n(TiO_2)_m$, wherein n/m is in the range of 20 to 200.

3. A process for preparing an epoxide according to claim 1, wherein the catalyst is present in the liquid phase as an aqueous suspension which has a pH between 5 and 9.

4. A process for preparing an epoxide according to claim 2, wherein the catalyst is present in the liquid phase as an aqueous suspension which has a pH between 5 and 9.

* * * * *